United States Patent
Herzog et al.

(10) Patent No.: US 6,579,824 B1
(45) Date of Patent: Jun. 17, 2003

(54) CATALYST BASED ON PALLADIUM, GOLD, ALKALI, AND LANTHANOID, AND A METHOD FOR PRODUCING VINYL ACETATE

(75) Inventors: Bernhard Herzog, Oberhausen (DE); Tao Wang, Corpus Christi, TX (US); Toan Nicolau, Corpus Christi, TX (US)

(73) Assignees: Celanese Chemicals Europe GmbH (DE); Celanese International Corporation

(*) Notice: Subject to any disclaimer, the term of this patent is extended or adjusted under 35 U.S.C. 154(b) by 0 days.

(21) Appl. No.: 09/581,452
(22) PCT Filed: Dec. 2, 1998
(86) PCT No.: PCT/EP98/07816
§ 371 (c)(1),
(2), (4) Date: Jul. 20, 2000
(87) PCT Pub. No.: WO99/29418
PCT Pub. Date: Jun. 17, 1999

(30) Foreign Application Priority Data

Dec. 11, 1997 (DE) .......................... 197 55 023

(51) Int. Cl.$^7$ ............................. B01J 23/52; B01J 23/58
(52) U.S. Cl. ...................... 502/302; 502/303; 502/304; 502/326; 502/330
(58) Field of Search ................................ 502/302, 303, 502/304, 326, 330

(56) References Cited

U.S. PATENT DOCUMENTS 5,591,688 A     1/1997  Blum et al.

FOREIGN PATENT DOCUMENTS

EP     0723810     7/1996
EP     0723811     7/1996

*Primary Examiner*—Paul J. Killos
(74) *Attorney, Agent, or Firm*—Bierman, Muserlian and Lucas

(57) ABSTRACT

The invention relates to a catalyst which contains palladium and/or compounds thereof, gold and/or compounds thereof, alkali metal compounds and at least one lanthanoid metal and/or compounds thereof. The invention also relates to the utilization of the catalyst in order to produce vinyl acetate from acetic acid, ethylene and oxygen or gases containing oxygen.

4 Claims, No Drawings

CATALYST BASED ON PALLADIUM, GOLD, ALKALI, AND LANTHANOID, AND A METHOD FOR PRODUCING VINYL ACETATE

This application is a 371 of PCT/EP98/027816 filed Dec. 2, 1998.

The present invention relates to a catalyst which comprises palladium and/or its compounds, gold and/or its compounds, alkali metal compounds and at least one lanthanoid metal and/or its compounds, and to its use for preparing vinyl acetate from acetic acid, ethylene and oxygen or oxygen-containing gases.

It is known that ethylene can be converted in the gas phase with acetic acid and oxygen or oxygen-containing gases on palladium/gold/alkali metal-containing fixed bed catalysts into vinyl acetate.

The palladium/gold/alkali metal-containing catalysts have a particular noble metal distribution, with the noble metals being present in a shell on the carrier particles, while the core of the particles is substantially free of noble metals. Catalysts with this noble metal distribution are distinguished by an increased specific productivity (g of vinyl acetate/g of noble metal). The noble metal compound in shell form is achieved by impregnation and subsequent precipitation of the noble metals using alkaline compounds.

The process disclosed in U.S. Pat. No. 4,048,096 for preparing palladium, potassium and gold-containing catalysts entails initial impregnation of the carrier material with an aqueous solution which comprises a mixture of palladium and gold salts. The metal salts are then converted by treatment with alkalis into water-insoluble compounds and are fixed on the carrier material in this way. Subsequent treatment with a reducing agent reduces the palladium and gold compounds to the corresponding metals. Finally, the carrier material loaded with palladium and gold is treated with an alkali metal acetate solution and dried. The impregnation step with the aqueous solution containing palladium and gold salts is characterized by the volume of the impregnation solution corresponding to the pore volume of the carrier material. The resulting catalyst has a shell structure in which palladium and gels are dispersed in a shell thickness of about 0.5 millimeter over the surface of the carrier material.

U.S. Pat. No. 3,775,342 also discloses a process for preparing palladium, potassium and gold-containing catalysts by impregnation with a solution of palladium and gold salts, by subsequent treatment with an alkali solution, which results in water-insoluble palladium and gold compounds precipitating on the carrier, and by subsequent reduction of the metal compounds to the corresponding noble metals. Treatment of the carrier material with an alkali metal acetate solution can take place before or after the reduction step.

U.S. Pat. No. 5,185,308 discloses a palladium, potassium and gold-containing shell catalyst in which the noble metals are dispersed in a shell thickness of 1 millimeter over the carrier material. The known catalyst has a ratio of gold to palladium in the range from 0.6 to 1.25 by weight.

It is further known to prepare a palladium, potassium and gold-containing shell catalyst by washing a carrier material, which has been provided with a binder, for example an alkali metal or alkaline earth metal carboxylate, before the impregnation with an acid, and treating with a base after the impregnation (EP-A-0 519 435).

In the process disclosed in U.S. Pat. No. 5,332,710 for preparing a palladium, gold and potassium-containing shell catalyst, the carrier impregnated with an aqueous palladium and gold salt solution is immersed in an aqueous fixing solution containing sodium hydroxide or potassium hydroxide and agitated therein for at least 0.5 h.

It has now been found, surprisingly, that catalysts of this type can be distinctly improved by adding at least one lanthanoid metal and/or a lanthanoid metal compound, i.e. provide a higher space-time yield with identical or higher selectivity for vinyl acetate.

The invention accordingly relates firstly to a process for preparing vinyl acetate in the gas phase from ethylene, acetic acid and oxygen or oxygen-containing gases on a catalyst which comprises 0.5–2.0% by weight of palladium and/or its compounds, 0.2–1.3% by weight of gold and/or its compounds, and 0.3–10% by weight of alkali metal compounds on a carrier, wherein the catalyst additionally comprises 0.01–1% by weight of at least one lanthanoid metal and/or its compounds, the percentages relating to the metal contents, based on the total mass of the catalyst.

The invention secondly relates to a catalyst which comprises 0.5–2.0% by weight of palladium and/or its compounds, 0.2–1.3% by weight of gold and/or its compounds, and 0.3–10% by weight of alkali metal compounds on a carrier, wherein the catalyst additionally comprises 0.01–1% by weight of at least one lanthanoid metal and/or its compounds, the percentages relating to the metal contents, based on the total mass of the catalyst.

The procedure for preparing the catalysts according to the invention is preferably as follows (U.S. Pat. Nos. 3,775,342, 4,048,096, 5,332,710):

(1) First the carrier particles are impregnated one or more times by being intimately mixed with at least one solution of at least one salt of the elements palladium and gold, and of at least one salt of at least one lanthanoid metal.

(2) The pretreated carrier is treated with a fixing solution with an alkaline reaction, which results in the noble metals and the lanthanoid metals being precipitated in the form of water-insoluble compounds on the surface of the carrier particles, and thus being fixed.

(3) The noble metal compounds deposited on the carrier particles are reduced to the corresponding metals by treatment with a reducing agent. A noble metal shell doped with at least one lanthanoid metal is produced in this way on the surface of the carrier particles.

(4) Interfering anions are removed by washing the treated catalyst.

(5) The treated catalyst is dried at not above 150° C.

(6) The dried carrier is treated with a solution which contains at least one alkali metal compound.

(7) Finally, the treated carrier is dried at not above 150° C.

The procedure in step (1) can also be to apply the salt solutions containing catalytically active substances to the carrier by single or multiple spraying on, vapor deposition or immersion.

The term "lanthanoid metals" means the 14 rare earth elements cerium, praseodymium, neodymium, promethium, samarium, europium, gadolinium, terbium, dysprosium, holmium, erbium, thulium, ytterbium and lutetium, and the elements scandium, yttrium and lanthanum because their chemical behavior resembles that of the rare earth elements.

Suitable carriers are the known inert carrier materials such as silica, alumina, aluminosilicates, silicates, titanium oxide, zirconium oxide, titanates, silicon carbide and carbon. Particularly suitable carriers of this type are those with a specific surface area of 40 to 350 m$^2$/g (measured by the BET method) and an average pore radius of 50 to 2000 Å (Angstrom) (measured by mercury porosimetry), especially silica ($SiO_2$) and $SiO_2/Al_2O_3$ mixtures. These carriers can be used in any form such as, for example, in the form of beads, tablets, rings, stars or particles of other shapes, with a diameter or length and thickness generally of 3 to 9 mm.

Carriers of these types can be prepared, for example, from aerogenic $SiO_2$ or an aerogenic $SiO_2/Al_2O_3$ mixture which can be prepared, for example, by flash hydrolysis of silicon tetrachloride or a silicon tetrachloride/-aluminum trichloride mixture in an oxyhydrogen flame (U.S. Pat. No. 3,939,199).

Suitable solvents for the palladium, gold, alkali metal and lanthanoid metal salts are all compounds in which the selected salts are soluble and which can easily be removed again after the impregnation by drying. Suitable for the acetates are, in particular, unsubstituted carboxylic acids having 2 to 10 carbon atoms such as acetic acid, propionic acid, n- and iso-butyric acid and the various valeric acids. Among the carboxylic acids, acetic acid is preferred because of its physical properties and also for economic reasons. Water is particularly suitable for the chlorides and chloro and acetato complexes. Additional use of another solvent is expedient if the salts are insufficiently soluble in acetic acid or in water. Thus, for example, palladium chloride can be dissolved considerably better in an aqueous acetic acid than in glacial acetic acid. Suitable additional solvents are those which are inert and are miscible with acetic acid or water. Those which may be mentioned as additions for acetic acid are ketones such as acetone and acetylacetone, also ethers such as tetrahydrofuran or dioxane, but also hydro-carbons such as benzene.

It is possible to apply a plurality of salts of palladium, gold, alkali metal and the particular lanthanoid metal, but generally exactly one salt of each of these elements is applied.

The elements palladium and gold which are to be applied in each case in the procedure of step (1), and the lanthanoid metal to be applied in each case, can be applied in the form of salt solutions, singly or else in any suitable combination in any suitable sequence, preferably using a single solution which contains these elements to be applied in the form of salts. It is particularly preferred to use a single solution which contains exactly one salt of each of these elements to be applied.

This solution preferably contains a salt of a single lanthanoid metal, but it is also possible to use a solution which contains one salt of each of different lanthanoid metals.

Where the following speaks generally of "the solution of the salts", the same applies analogously to the case where a plurality of solutions are employed in sequence, each of which contains only part of the totality of salts to be applied, in which case the total of the individual parts amounts to the total quantity of the salts to be applied to the carrier.

For the procedure of step (1), the solution of the salts is applied to the carrier particles by impregnating the latter one or more times with this solution, employing the total volume of the solution all at once or divided into two or more part-volumes. However, it is expedient to use the total volume of the salt solution all at once, so that the carrier particles are impregnated with the required amount of elements to be applied by a single impregnation, in which case drying can follow immediately. In the case of impregnation sequentially with a plurality of part-volumes, drying is carried out immediately after each impregnation.

"Immediate" drying means in this connection that drying the impregnated particles must start without delay. It is generally sufficient for this case to start drying the particles no later than half an hour after the end of an impregnation.

The impregnation of the carrier particles with the solution of the salts to be applied is carried out by covering the carrier particles with the solution and, where appropriate, then pouring off or filtering off excess solution. It is advantageous, with regard to losses of solution, to employ only the quantity of solution corresponding to the integral pore volume of the catalyst carrier.

It is expedient to mix the carrier particles intimately during the impregnation, for example in a rotating or agitated flask or a mixing drum, in which case drying can follow immediately. The speed of rotation or intensity of the agitation must, on the one hand, be sufficient to ensure good mixing and wetting of the carrier particles but must, on the other hand, not be so great that there is considerable abrasion of the carrier material.

The solution of the salts should have a temperature which is high enough to prevent the salts precipitating during the application to the carrier. The temperature should, however, generally not be much above 70° C. in order to avoid excessive evaporation of the solvent and decomposition of the noble metal compounds.

The treatment of the carrier particles impregnated in step (1) with a solution with an alkaline reaction converts the salts of the applied elements into water-insoluble compounds, and they are thus fixed to the surface of the carrier (step (2)).

Examples of fixing solutions which can be used are aqueous solutions with an alkaline reaction. Examples of such solutions are aqueous solutions of alkali metal silicates, alkali metal carbonates and bicarbonates or alkali metal hydroxides.

An aqueous solution of the alkali metal hydroxides, in particular potassium or sodium hydroxide, is preferred. Aqueous solutions which contain boron compounds can also be used as solutions with an alkaline reaction. Particularly suitable in this case are aqueous solutions of borax, potassium tetraborate or mixtures of alkali metal hydroxide solution and boric acid. The alkaline solution may have buffering properties.

The amount of the compound with an alkaline reaction present in the fixing solution is expediently such that it is at least sufficient for stoichiometric conversion of the applied palladium, gold and lanthanoid metal salts into water-insoluble compounds.

However, it is also possible to use an excess of the compound with an alkaline reaction present in the fixing solution, the excess generally being 1 to 10 times the amount required by the stoichiometry.

The volume of the fixing solution must be at least sufficient to cover the impregnated carrier completely with the fixing solution. The fixing preferably takes place by the rotation immersion technique disclosed in U.S. Pat. No. 5,332,710, which is incorporated herein by reference. This technique comprises agitating the carrier which is completely covered by the fixing solution by rotation from the start of the treatment with the fixing solution.

Every type of rotation or similar treatment which keeps the carrier particles agitated can be used, because the exact manner is not critical. The intensity of the agitation is important, however. It should be sufficient for the entire surface area of the impregnated carrier to be wetted uniformly with the alkaline fixing solution.

The treated carrier is then left to stand in the fixing solution at room temperature for up to 16 hours in order to ensure that the applied palladium, gold and lanthanoid metal salts are completely precipitated in the form of water-insoluble compounds on the catalyst carrier.

The reaction on the carrier can, however, also be carried out at elevated temperature, for example at 70° C.

After the fixation is complete, the supernatant fixing solution is poured away. This can be followed, where appropriate, by washing the treated carrier in order to remove the soluble compounds present on the treated carrier, for example the alkali metal chlorides liberated in the fixing step and any excess which is present of the compound with an alkaline reaction present in the fixing solution, by washing.

For this purpose, the treated carrier is continuously washed with the washing liquid, preferably with running demineralized water, at room temperature. The washing is continued until interfering anions, for example chlorides, are substantially removed from the carrier.

The moist impregnated catalyst carrier can then be dried, which is expedient if the subsequent reduction of the deposited noble metal compounds to the corresponding metals (step (3)) is carried out in the gas phase.

Reduction of the water-insoluble compounds fixed on the catalyst carrier to the corresponding metals can be carried out with a gaseous reducing agent (step (3)).

The reduction temperature is generally between 40 and 260° C., preferably between 70 and 200° C. It is generally expedient to use for the reduction a reducing agent which is diluted with inert gas and contains 0.01 to 50% by volume, preferably 0.5 to 20% by volume, of reducing agent. It is possible to use as inert gas, for example, nitrogen, carbon dioxide or a noble gas. Examples of suitable reducing agents are hydrogen, methanol, formaldehyde, ethylene, propylene, isobutylene, butylene or other olefins. The reduction can also be carried out in liquid phase at a temperature from 0° C. to 90° C., preferably from 15 to 25° C. Examples of reducing agents which can be used are aqueous solutions of hydrazine, formic acid or alkali metal borohydrides, preferably sodium borohydride. The amount of reducing agent depends on the amount of the noble metals; the reduction equivalent should be at least equal to oxidation equivalent in quantity, but larger amounts of reducing agent are not harmful.

It is essential to select the reduction conditions in the reduction step so that the fixed water-insoluble noble metal compounds are reduced to the corresponding noble metals. It is, on the other hand, immaterial whether the fixed water-insoluble lanthanoid metal compounds are also converted under the selected reduction conditions into the corresponding lanthanoid metals, because it is not critical for the suitability of the novel catalysts for preparing vinyl acetate whether the lanthanoid metals are present as elements and/or their compounds in the noble metal shell of the novel catalysts.

If no washing step takes place after the fixation is complete (step (2)), or if the reduction takes place with an aqueous solution of a reducing agent, the treated catalyst carrier must, after the reduction is complete, be washed several times to remove interfering compounds, for example to remove chloride residues derived from the impregnation step and released due to the fixation and reduction of the noble metals (step (4)).

For this purpose, the treated carrier is washed continuously with the washing liquid, preferably with running demineralized water, at room temperature until interfering anions, for example chlorides, are removed.

If an aqueous solution of a reducing agent is used in step (3), residues of the reducing agent used can also be removed with the washing step.

The catalyst is then dried at temperatures not exceeding 150° C. (step (5)).

In step (6), the dried catalyst carrier is then treated, preferably impregnated, one or more times with a solution of an alkali metal compound, the total volume of the solution being employed all at once or divided into part-volumes. However, it is expedient to use the total volume of the solution all at once, so that the carrier particles are impregnated with the required amounts of alkali metal compound to be applied by a single impregnation. The volume of the solution of the alkali metal compound is, in the case of single or multiple impregnation, generally between 60 and 110%, preferably between 80 and 100%, of the pore volume.

The solution of the alkali metal compound can also be applied to the carrier by single or multiple spraying on, vapor deposition or immersion.

After the treatment with a solution of an alkali metal compound, the catalyst carrier is finally dried at no higher than 150° C. (step (7)).

The alkali metal compound is used in an amount such that the catalyst carrier contains 0.1 to 10% by weight of alkali metal after the drying.

The drying of the treated catalyst carrier to be carried out in steps (5) and (7) takes place in a stream of hot air or in a stream of inert gas, for example in a stream of nitrogen or carbon dioxide. The temperature during this drying should generally be 60 to 150° C., preferably 100 to 150° C. Drying is moreover carried out, where appropriate, under reduced pressure, generally from 0.01 MPa to 0.08 MPa.

If the drying forms part of step (1) and, where appropriate, the other steps, the procedure is the same.

The finished shell catalysts containing palladium, gold, alkali metal and at least one lanthanoid metal have the following metal contents:

| | |
|---|---|
| Palladium content: | generally 0.5–2.0% by weight, preferably 0.6–1.5% by weight; |
| Gold content: | generally 0.2–1.3% by weight, preferably 0.3–1.1% by weight; |
| Alkali metal content: and potassium is preferably used. | generally 0.3–10% by weight, |
| Potassium content: | generally 0.5–4.0% by weight, preferably 1.5–3.0% by weight; |
| Lanthanoid metal content: | generally 0.01–1% by weight, preferably 0.05–0.5% by weight. |

If more than one lanthanoid metal is used to dope the palladium, gold and alkali metal-containing shell catalysts, the term "lanthanoid metal content" means the total content of all the lanthanoid metals present in the finished catalyst. The stated percentages always relate to the amounts of the elements palladium, gold, alkali metal and lanthanoid metal present in the catalyst, based on the total mass of the catalyst (active elements plus anions plus carrier material).

Suitable salts are all salts of palladium, gold, an alkali metal and a lanthanoid element which are soluble; the acetates, the chlorides, and the acetato and chloro complexes are preferred. However, in the case of interfering anions such as, for example, in the case of chlorides, it must be ensured that these anions are substantially removed before use of the catalyst. This takes place by washing the doped carrier, for example with water, after, for example, the palladium and gold which have been applied as chloride have been converted into an insoluble form, for example through the fixation with compounds having an alkaline reaction and/or by reduction (steps (2) and (3)).

Particularly suitable salts of palladium and gold are chloride, chloro complexes and carboxylates, preferably the salts of aliphatic monocarboxylic acids having 2 to carbon atoms, for example the acetate, propionate or butyrate. Further suitable examples are the nitrate, nitrite, oxide hydrate, oxalate, acetylacetonate or acetoacetate. Because of the good solubility and availability, preferred palladium and gold salts are in particular the chlorides and chloro complexes of palladium and gold.

The alkali metal compound preferably employed is at least one sodium, potassium, rubidium or caesium compound, in particular a potassium compound. Particularly suitable compounds are carboxylates, in particular acetates and propionates. Compounds which are converted under the reaction conditions into the alkali metal acetate, such as, for example, the hydroxide, the oxide or the carbonate, are also suitable.

The lanthanoid metal compound employed is preferably at least one praseodymium, neodymium, samarium, europium or dysprosium compound. However, it is also possible to employ mixtures of these compounds.

The chlorides, nitrates, acetates and acetylacetonates are particularly suitable as lanthanoid metal compound.

In the novel catalysts, the noble metals and the particular lanthanoid metals and/or their compounds are applied in a shell on the carrier particle.

Vinyl acetate is generally prepared by passing acetic acid, ethylene and oxygen-containing gases at temperatures from 100 to 220° C., preferably 120 to 200° C., under pressures from 0.1 to 2.5 MPa, preferably 0.1 to 2.0 MPa, over the finished catalyst, it being possible to circulate unreacted components. It is also advantageous in some circumstances to dilute with inert gases such as nitrogen or carbon dioxide. Carbon dioxide is particularly suitable for the dilution because it is formed in small amounts during the reaction.

With the same reaction conditions it is possible with the aid of the novel catalysts to prepare more vinyl acetate per reactor volume and time with, at the same time, improved selectivity by comparison with known catalysts.

This facilitates the workup of the resulting crude vinyl acetate because the vinyl acetate content in the gas discharged from the reactor is higher, which further results in a saving of energy in the workup part. A suitable workup is described, for example, in U.S. Pat. No. 5,066,365.

If, on the other hand, it is wished to keep the spacetime yield constant, it is possible to reduce the reaction temperature and thus carry out the reaction more selectively, with the same total productivity, in which case there is a saving of precursors. This is also associated with a decrease in the amount of carbon dioxide, which is formed as byproduct and therefore must be removed, and in the loss of entrained ethylene which is associated with this removal. In addition, this procedure results in an increase in the useful life of the catalyst.

The following examples are intended to illustrate the invention but do not restrict it. The percentages of the elements palladium, gold, potassium and of the lanthanoid element are percent by weight based on the total mass of the catalyst.

The catalyst carrier used was the $SiO_2$ carrier available from Süd-Chemie with the name KA 160 in the form of beads with a diameter of 5 mm. The pore volume of 1 l of carrier was 335 ml.

EXAMPLE 1

5.37 g (=0.0164 mol) of potassium tetrachloropalladate, 3.36 g (0.0089 mol) of potassium tetrachloroaurate and 0.74 g (0.0018 mol) of praseodymium trinitrate pentahydrate were weighed out together and dissolved in 90 ml of demineralized water (solution volume=100% of the pore volume). With gentle agitation, this solution was completely adsorbed onto 147.5 g of the carrier material at room temperature. To precipitate insoluble palladium, gold and praseodymium compounds, which leads to formation of a noble metal shell, the pretreated carrier was mixed with a solution of 3.1 g of sodium hydroxide in 300 ml of demineralized water. Immediately after addition of the alkaline fixing solution, the carrier was agitated in a rotary evaporator rotating at a rate of 5 revolutions per minute (rpm) for a period of 2.5 hours. To complete the precipitation, the mixture was left to stand at room temperature for a period of 14 hours. The supernatant solution was then poured off, and the mixture was washed with demineralized water until free of chloride. A water flow rate of 200 ml/minute for approximately 5 hours was necessary for this. To check for freedom from chloride, a silver nitrate solution was added to the washing water and it was examined for silver chloride precipitation. The catalyst was subsequently dried at a temperature of 100° C. for a period of 2 hours. It was then reduced with a gas mixture consisting of 5% by volume ethylene and 95% by volume nitrogen, passing this gas mixture over the catalyst at a temperature of 150° C. for a period of 5 hours. The reduced catalyst was then impregnated with a solution of 10 g of potassium acetate in 75 ml of demineralized water (solution volume=83% of the pore volume) in portions and dried with hot air at a temperature of 100° C. for a period of 2 hours.

The finished catalyst contained 1.1% by weight Pd, 1.1% by weight Au, 2.5% by weight K and 0.16% by weight Pr.

EXAMPLE 2

The procedure was analogous to that of Example 1 but the lanthanoid metal compound used was 0.71 g (0.0017 mol) of samarium trinitrate pentahydrate in place of praseodymium trinitrate pentahydrate.

The finished catalyst contained 1.1% by weight Pd, 1.1% by weight Au, 2.5% by weight K and 0.16% by weight Sm.

EXAMPLE 3

The procedure was analogous to that of Example 1 but 0.7 g (0.0016 mol) of europium trinitrate pentahydrate was used as lanthanoid metal compound.

The finished catalyst contained 1.1% by weight Pd, 1.1% by weight Au, 2.5% by weight K and 0.15% by weight Eu.

EXAMPLE 4

The procedure was analogous to that of Example 1 but 0.34 g (0.0008 mol) of neodymium trinitrate pentahydrate was used as lanthanoid metal compound.

The finished catalyst contained 1.1% by weight Pd, 1.1% by weight Au, 2.5% by weight K and 0.07% by weight Nd.

EXAMPLE 5

The procedure was analogous to that of Example 1 but 0.3 g (0.0008 mol) of dysprosium trichloride hexahydrate was used as lanthanoid metal compound.

The finished catalyst contained 1.1% by weight Pd, 1.1% by weight Au, 2.5% by weight K and 0.08% by weight Dy.

EXAMPLE 6

The procedure was analogous to that of Example 5 but 0.6 g (0.0016 mol) of dysprosium trichloride hexahydrate was used.

The finished catalyst contained 1.1% by weight Pd, 1.1% by weight Au, 2.5% by weight K and 0.16% by weight Dy.

COMPARATIVE EXAMPLE 1a

The procedure was as in Example 1 but no lanthanoid metal salts were added to the impregnation solution containing potassium tetrachloropalladate and potassium tetrachloroaurate.

The finished catalyst contained 1.1% by weight Pd, 1.1% by weight Au and 2.5% by weight K.

The novel catalysts prepared as in Examples 1–6, and the known catalyst prepared as in Comparative Example 1a, were tested in a Berty reactor. The average temperature of the jacket of the Berty reactor was chosen so that a constant oxygen conversion of 45% was observed.

The results are to be found in the table.

| Example | Space-time yield | $CO_2$ selectivity |
| --- | --- | --- |
| 1 | 793 | 8.97 |
| 2 | 780 | 9.23 |
| 3 | 802 | 8.79 |
| 4 | 726 | 8.50 |
| 5 | 733 | 9.0 |
| 6 | 722 | 9.3 |
| Comparative Example 1a | 683 | 10.9 |

Space-time yield in gram of vinyl acetate per liter of catalyst and hour.

$CO_2$ selectivity in % based on the amount of ethylene reacted.

It was found, surprisingly, that even small additions of lanthanoid metals to the known palladium, gold and potassium-containing catalysts distinctly improve the $CO_2$ selectivity and the productivity (space-time yield) of these catalysts in preparing vinyl acetate.

What is claimed is:

1. A catalyst comprising 0.2 to 1.3% by weight of gold or a gold compound calculated as gold metal, 0.3 to 10% by weight of an alkali metal compound calculated as alkali metal, 0.5 to 2.0% by weight of palladium or palladium compound calculated as palladium metal and 0.01 to 1% by weight of at least one lanthanoid compound or metal calculated as lanthanoid metal on a carrier, the metal percentage based on the total mass of the catalyst.

2. A catalyst of claim 1 containing at least one potassium compound.

3. A catalyst of claim 1 wherein the amount of lanthanoid compound or metal is 0.05 to 0.5% by weight calculated as lanthanoid metal.

4. A catalyst of claim 1 wherein the lanthanoid metal is selected from the group consisting of praseodymium, samarium, europium, neodymium and dysprosium.

* * * * *